United States Patent [19]

Fukuchi

[11] Patent Number: 4,948,956

[45] Date of Patent: Aug. 14, 1990

[54] APPARATUS WITH AREA-MASKING FOR DETECTING DEFECTS ON BOTTLE SIDEWALLS

[75] Inventor: Hiroyuki Fukuchi, Yokohama, Japan

[73] Assignee: Kirin Beer Kabushiki Kaisha, Tokyo, Japan

[21] Appl. No.: 357,288

[22] Filed: May 26, 1989

[30] Foreign Application Priority Data

May 27, 1988 [JP] Japan .............................. 63-128247

[51] Int. Cl.$^5$ ........................... G01N 9/04; H04N 7/18
[52] U.S. Cl. ................................ 250/223 B; 250/563; 356/240; 358/106
[58] Field of Search .................... 250/223 B, 563, 562; 356/240; 382/8, 27; 358/106

[56] References Cited

U.S. PATENT DOCUMENTS

| | | | |
|---|---|---|---|
| 3,887,762 | 6/1975 | Uno et al. ............................ | 358/106 |
| 4,376,951 | 3/1983 | Miyazawa ............................ | 356/240 |
| 4,506,382 | 3/1985 | Hada et al. ............................ | 382/27 |
| 4,549,205 | 10/1985 | Misaki et al. ..................... | 250/223 B |
| 4,742,399 | 5/1988 | Kitamura ............................ | 382/27 |
| 4,831,250 | 5/1989 | Fukuchi et al. ................. | 250/223 B |

FOREIGN PATENT DOCUMENTS 2096763  10/1982  United Kingdom ............ 250/223 B Primary Examiner—David C. Nelms
Assistant Examiner—Michael Messinger
Attorney, Agent, or Firm—Fleit, Jacobson, Cohn, Price, Holman & Stern

[57] ABSTRACT

An apparatus for detecting defects on bottle sidewalls is disclosed. The apparatus for detecting defects on bottle sidewalls comprises: illumination means for illuminating the sidewall of a bottle; photoelectrically converting means for photoelectrically converting an image of lights transmitted through the sidewall of the bottle illuminated by the illuminating means; defect detecting means for inspecting the transmitted light image photoelectrically converted by the photoelectrically converting means for any defects to detect defects based on brightnesses of at least two points; area-masking means for setting a masking area corresponding to a point to be noted in the transmitted light image, and outputting an area masking signal indicating that the point to be noted is a defect point, based on a distribution of defect points in the masking area; and judging means for judging the presence of a defect on the sidewall of the bottle, based on the area masking signal from the area masking means. The apparatus for detecting defect on bottle sidewalls can detect with high precision opaque defects which are thin and extend over large areas.

28 Claims, 11 Drawing Sheets

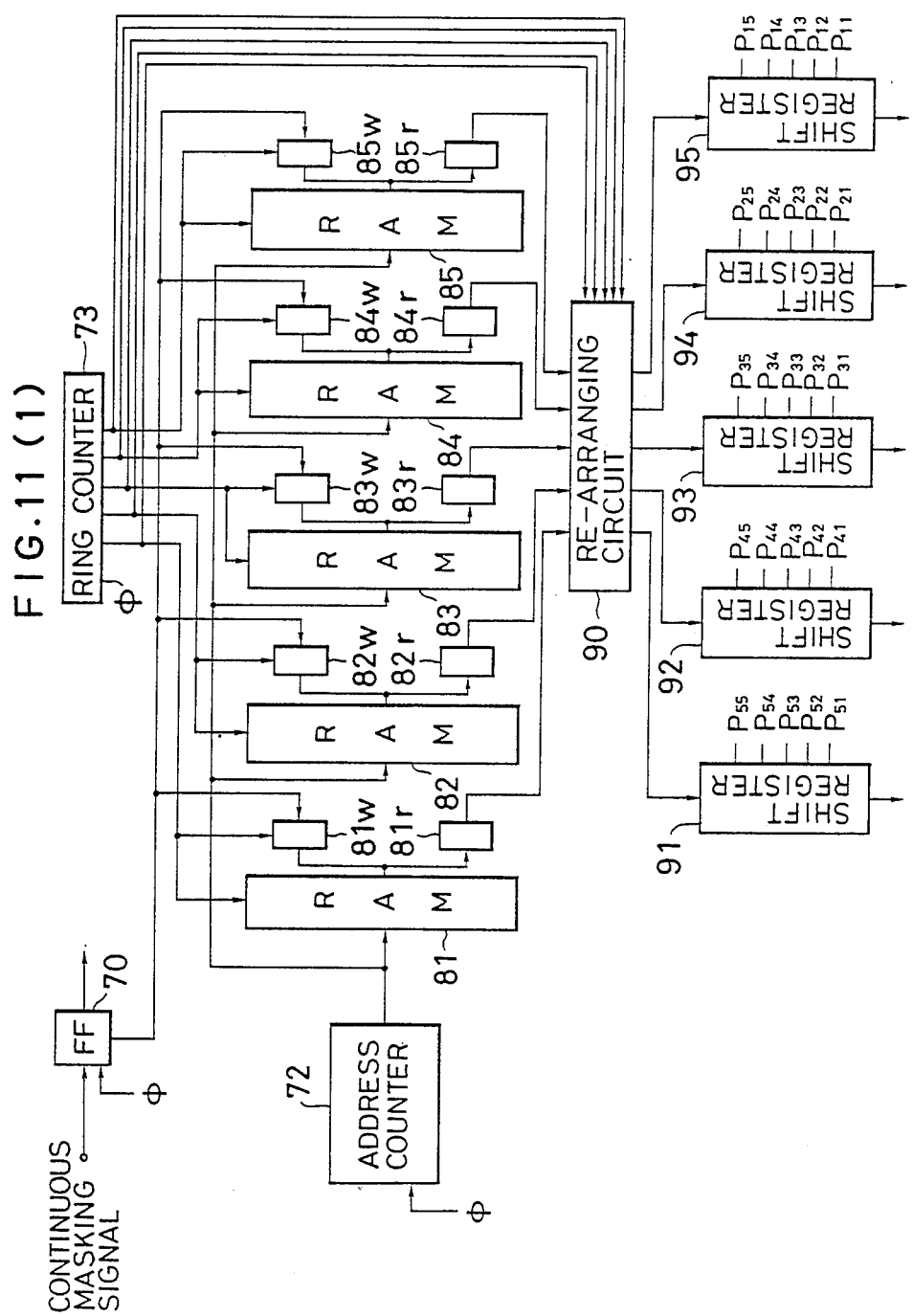
FIG. 11 (1)

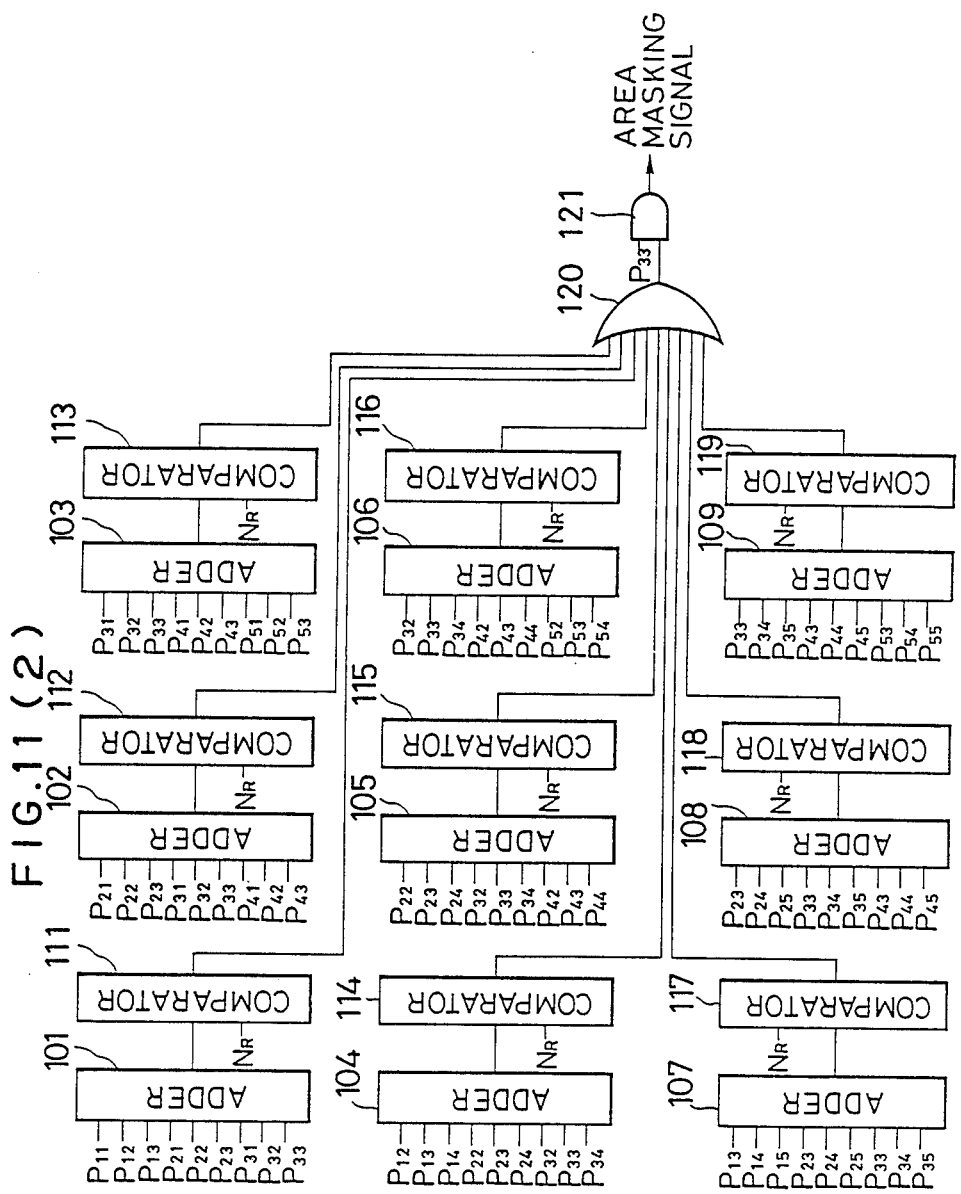

APPARATUS WITH AREA-MASKING FOR DETECTING DEFECTS ON BOTTLE SIDEWALLS

BACKGROUND OF THE INVENTION

This invention relates to an apparatus for detecting defects on the sidewalls of bottles.

It is necessary to inspect glass bottles containing liquors, beverages, foods, etc. for any defects whether they are newly made or have been recovered for reuses. The bottles are inspected on parts thereof, i.e., the bodies or sidewalls, bottoms, tops of the mouths and threaded bottle necks. Among these parts, the sidewalls tend to have defects, such as foreign matters or smears which may cause sanitary problems, and cracks, scraches, seeds, blisters, etc. which may cause bottle breakages. It is necessary to inspect the bottles accurately for any of these defects.

Generally the apparatus for detecting defects on bottle sidewalls utilizes the fact that a portion of a defect appears darker than the other portion, in inspecting the sidewalls for defects. This apparatus has found it easy to detect defects, such as opaque foreign matters, etc. which are very light blocking, but has found it difficult to detect accurately defects, such as light smears, streaks, blisters, etc. which are opaque and are extended over large areas. That is, a problem with this generally used apparatus is that when the sensitivity of a photoelectric device is increased to detect these opaque large defects, even noises due to different colors, different thicknesses of the sidewalls, etc. are detected as defects.

SUMMARY OF THE INVENTION

A first object of this invention is to provide an apparatus for detecting defect on bottle sidewalls which can detect with high precision opaque defects which are thin and extend over large areas.

A second object of this invention is to provide an apparatus for detecting defects on bottle sidewalls which can detect opaque defect which are thin and extend over large areas, without changing their contours.

The first object can be achieved by an apparatus for detecting defects on bottle sidewalls comprising: illumination means for illuminating the sidewall of a bottle; photoelectrically converting means for photoelectrically converting an image of lights transmitted through the sidewall of the bottle illuminated by the illuminating means; defect detecting means for inspecting the transmitted light image photoelectrically converted by the photoelectrically converting means for any defects to detect defects based on brightnesses of at least two points; area-masking means for setting a masking area corresponding to a point to be noted in the transmitted light image, and outputting an area masking signal indicating that the point to be noted is a defect point, based on a distribution of defect points in the masking area; and judging means for judging the presence of a defect on the sidewall of the bottle, based on the area masking signal from the area masking means.

The second object can be achieved by an apparatus for detecting defects on bottle sidewalls comprising: illumination means for illuminating the sidewall of a bottle; photoelectrically converting means for photoelectrically converting an image of lights transmitted through the sidewall of the bottle illuminated by the illuminating means; defect detecting means for inspecting the transmitted light image photoelectrically converted by the photoelectrically converting means for any defects to detect defects based on brightnesses of at least two points: area masking means for setting a masking area corresponding to a point to be noted in the transmitted light image, setting in the masking area a plurality of smaller masking areas containing the point to be noted and being smaller than the masking area, finding the point to be noted a defect point when a number of defect points in one of the smaller masking areas is above a set value, and outputting an area masking signal indicating that the point to bc noted is a defect point; and judging means for judging the presence of a defect on the sidewall of the bottle, based on the area masking signal from the area masking means.

BRIEF DESCRIPTION OF THE DRAWINGS

FIGS. 11(1) and 11(2) are circuit& diagrams exemplifying the area masking circuit of the apparatus for detecting detects on bottle sidewalls of FIG. 7;

DETAILED DESCRIPTION OF THE INVENTION

Figure 1:
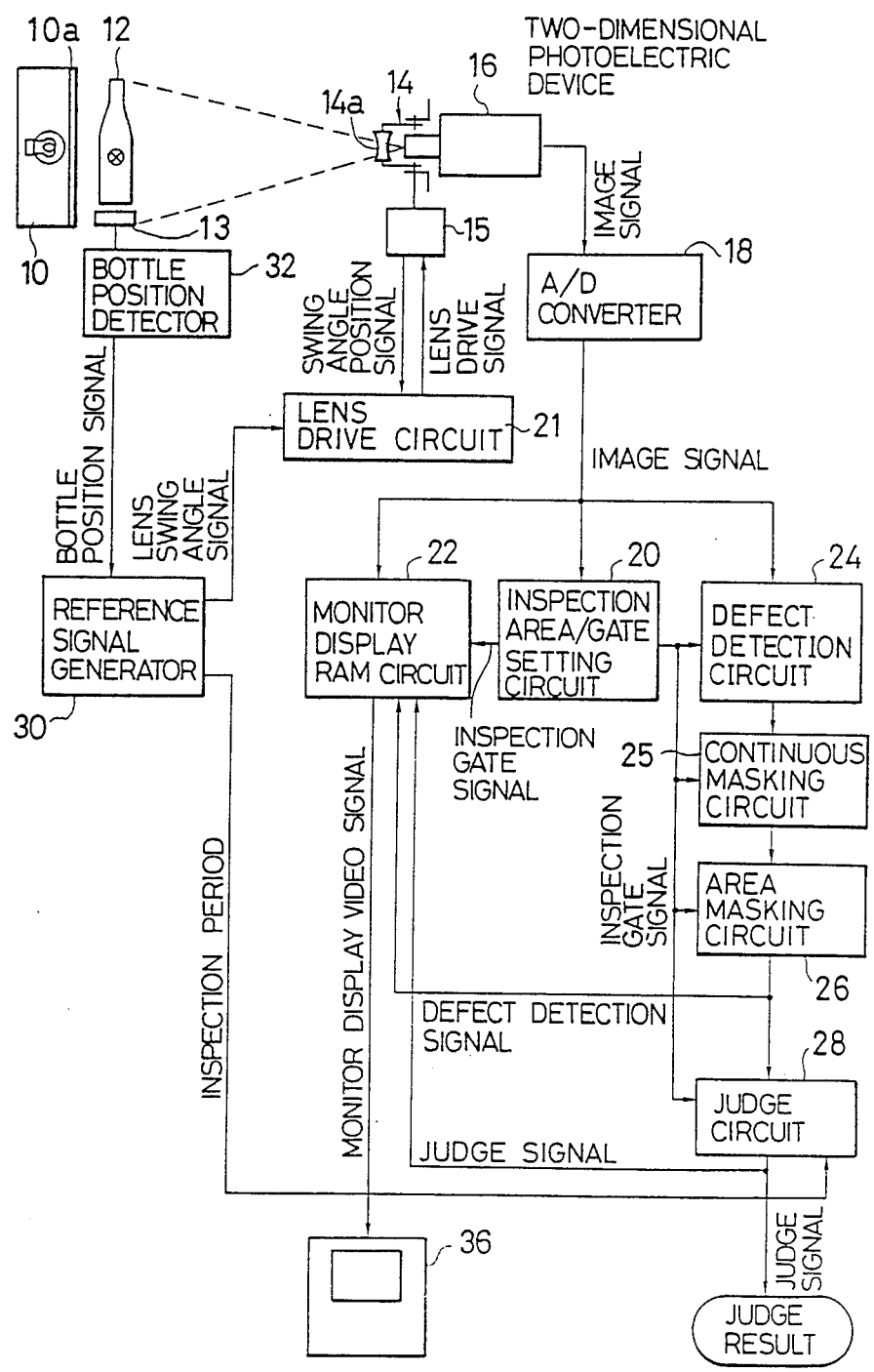
FIG. 1 is a block diagram of the apparatus for detecting defects on bottle sidewalls according to a first embodiment of this invention.

FIG. 1 shows the apparatus for detecting defects on bottle sidewalls according to a first embodiment of this invention.

In this embodiment, a bottle 12 to be inspected is continuously conveyed on rotation. The bottle 1 is illuminated by a diffusion light source 10 having a surface for emitting even diffused lights. A diffusion plate 1Oa for diffusing the illumination light is disposed on the front of the diffusion light source 1O. An image of lights transmitted through the sidewall of the bottle 12 is formed in a two-dimensional photoelectric device 16. The two-dimensional photoelectric device 16 comprises a light detecting unit, such as an area CCD, for converting the transmitted light image into an electric analog signal, and an optical system for forming the transmitted light image of the bottle 12.

The optical axis changing unit 14 is disposed in the optical axis of the two-dimensional photoelectric device 16 on the side nearer to the bottle 12 and changes the optical axis of the optical system with respect to the light detecting unit of the two-dimensional photoelectric device 16. The optical axis changing unit 14 changes the optical axis in synchronization with a movement of the bottle 12 so that a transmitted light image of the bottle 12 is formed in the light detecting unit of the two-dimensional photoelectric device 16. Specifically, a drive motor 15 swings horizontally a lens 14a disposed on the front of the two-dimensional photoelectric device 16 by a lens driving circuit 21 to change the optical axis.

An A/D converter 18 converts an analog image signal from the two-dimensional photoelectric device 16 into a digital image signal of a given bits. This digital image signal is supplied to an inspection area/gate setting circuit 20, a monitor display RAM circuit 22 and a defect detection circuit 24.

Figure 2:
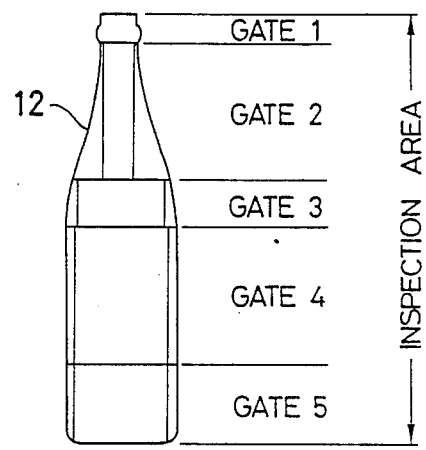
FIG. 2 is a view showing an inspection area and inspection gates for the apparatus for detecting defects on bottle sidewalls of FIG. 1.

The inspection area/gate setting circuit 20 is for setting inspection areas in which the defect detection circuit 24, which will be explained below, detects defects based on the transmitted light image as shown in FIG. 2. The inspection area may be determined based on the edges of the transmitted light image of the bottle 12 or may be fixedly determined beforehand. In FIG. 2, the inspection area is set on the entire bottle 12, and the inspection area is divided in five inspection gates 1, 2, 3, 4, 5 in accordance with the profile of the bottle 12. The inspection area/gate setting circuit 20 supplies an inspecting gate signal to the monitor display RAM circuit 22, the defect detection circuit 24, a continuous masking circuit 25, an area masking circuit 26 and a judge circuit 28.

Based on the digital image signal from the A/D converter 18, the defect detection circuit 24 compares in brightness a plurality of points spaced from each other vertically and horizontally by a given distance to detect defects. The defect detection circuit 24 outputs a defect detection signal of "1" when a defect is present and outputs a defect detection signal of "0" when a defect is absent.

The defect detecting system for comparing a plurality of points in brightness includes a two-point defect detection system in which two points are compared in brightness to detect a defect, and a three-point detecting system in which three points are compared in brightness to detect a defect.

In the two-point defect detecting system, when the following formula $$|QA-QB| \geqq \text{(constant A)}$$

is satisfied, where two points A and B have brightnesses QA and QB respectively, a defect is present.

The three-point defect detecting system enables a defect to be detected without failure even when a transmitted light has uneven brightness. In this three-point point defect detecting system, when the following formula $$|QB-\{(QA+QC)/2\}| \geqq \text{(constant B)}$$

is satisfied, where three points A, B and C have brightnesses QA, QB, QC respectively, a defect is present.

It is also possible to detect a defect, based on a ratio between brightnesses QA and QB of two points A and B to be compared for detection. That is, when one of the following formulas $$QA/QB \geqq \text{(constant B)}$$

$$QA/QB \geqq \text{(constant C)}$$

is satisfied, a defect is present.

It is also possible to detect a defect when one of the following formulas $$QB/\{(QA+QC)/2\} \geqq \text{(constant D)}$$

$$QB/\{(QA+QC)/2\} \geqq \text{(constant D)}$$

are satisfied, where three points A, B and C have brightnesses QA, QB and QC, a defect is present.

A defect detection signal outputted by the defect detection circuit 24 is subjected to continuous masking by the continuous masking circuit 25. When the defect detecting circuit 24 increases the sensitivity for the prevention of a defect detection error, sometimes the circuit 24 erroneously detects none defective points as defect points. The continuous masking is for removing such erroneous defect points. At an actual defect appears continuous defect points having a size corresponding to that of the actual defect. Contrary to this, at a non-defect appears separate defect points. In this continuous masking, separate defect points, and defect points which are continuous only below a set value are removed as actually nondefects, and the continuous masking circuit 25 outputs a fresh continuous masking signal at each point. For example, when a defect point is actually a defect, a continuous masking signal of "1" is outputted, and when the defect point is not a defect, a continuous masking signal of "0" is outputted.

Figure 3:
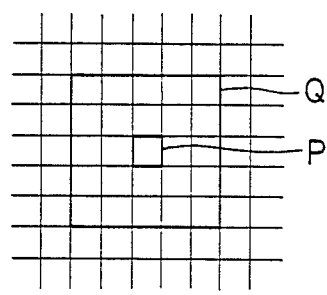
FIG. 3 is a view showing a masking area of an area masking circuit of the apparatus for detecting defects on bottle sidewalls of FIG. 1.

A continuous masking signal outputted by the continuous masking circuit 25 is subjected to the area masking by an area masking circuit 26. In the area masking, as shown in FIG. 3, a rectangular masking area Q of 5 rows × 6 columns is set with each point P centered, a number of points in the area Q at which (points) continuous masking signals are defects are added, and, based on whether or not a total number of defect points exceeds a set value, the area masking circuit 26 outputs an area masking signal. That is, an area masking signal is generated only at a portion on which continuous masking signals are concentrated with noises appearing separately being removed.

Figure 4:
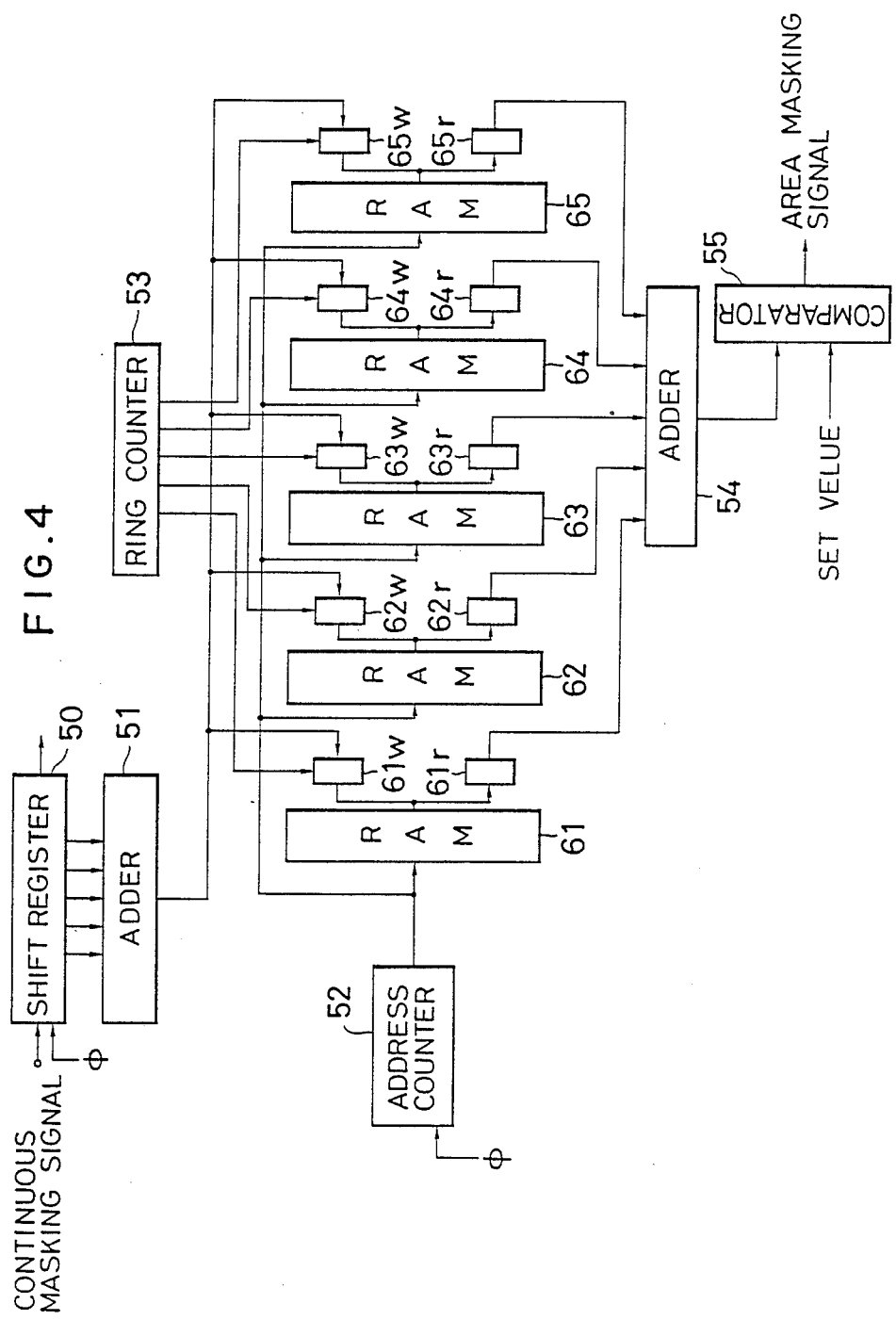
FIG. 4 is a circuit diagram exemplifying the area masking circuit of the apparatus for detecting defect on bottle sidewalls of FIG. 1.

FIG. 4 is an example of the area masking circuit 25.

Figures 5, 6A, 6B:
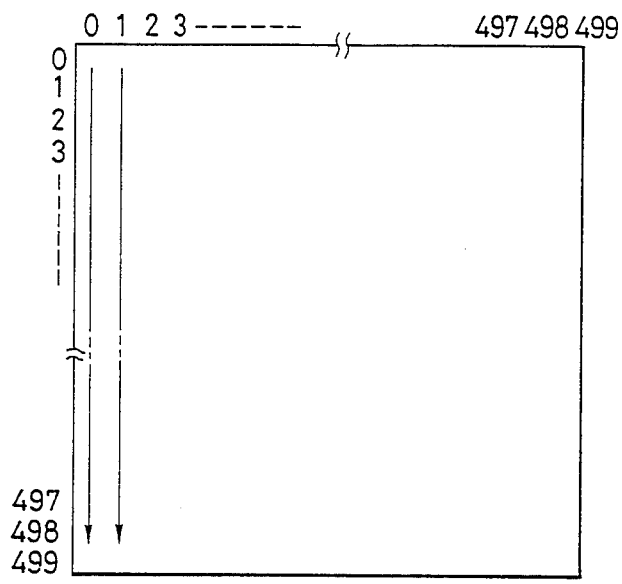
FIG. 5 is a view explaining the operation of the area masking circuit.
FIGS. 6(a) and 6(b) are views showing results of masking noises and opaque defects in an image of light transmitted through a bottle sidewall.

A continuous masking signal for each image is consecutively inputted to a shift register 50 in synchronization with a clock pulse $\phi$ to be shifted and outputted. The digit number of the shift register 50 corresponds to a number of rows of the masking area Q. In the case where a screen has 500 pixels x 500 pixels as shown in FIG. 5, continuous masking signals are inputted to the shift register 50 first at the upper left end and then vertically downward. The shift register 50 has an adder 51 which adds the values of 5 continuous masking signals. That is, a sum given by the adder 51 gives a sum of the continuous masking signals on each column of the masking region Q.

There are provided five RAMs 61, 62, 63, 64, 65 each having a capacity of 500 bits corresponding to the length of the vertical length of the screen. A number of the RAMs 61-65 corresponds to a number of columns of the masking area Q. Addresses to the RAMs 61-65 are generated by an address counter 52. Data are written in the RAMs 61-65 through respective write gates 61w-65w. It is designated by an output of a quinary ring counter 53 which write gate 61w-65w data is written in. The ring counter 53 counts up by one every time the address counter 52 has outputted addresses from 0 to 499.

A sum given by the adder 51 is written in bits of an address of one of the RAMs 61-65 designated by the ring counter 65. The address of the RAMs 61-65 has been generated by the address counter 52. Accordingly the RAMs 61-65 store sums for every five vertically located continuous masking signals for adjacent five columns of the screen.

Data are read from the RAMs 61-65 through read gates 61r-65r. All the read gates 61r-65r are kept opened when data are read, so that the data of all the RAMs 61-65 including data being currently written are simultaneously read to be outputted to an adder 54.

The adder 54 adds the data read from the RAMs 61-65 and outputs an addition result to a comparator 55. Since the RAMs 61-65 correspond to the columns of the masking area Q, the addition result given by the adder 55 is a sum of all the continuous masking signals in the masking area Q. The comparator 55 compares this addition result with a set value to output a comparison result as an area masking signal. For example, when the set value is 18, the area masking signal becomes "1" only when the continuous masking signals of 18 or more points in the 5×5 masking area Q are "1", and when less than 18 points have "1", the area masking signal becomes "0".

The area masking circuit shown in FIG. 4 enables an area masking signal given by area-masking the 5×5 masking area to be obtained in real time only by inputting continuous masking signals consecutively in the shift register 50.

The judge circuit 28 judges the presence of a defect, based on an area masking signal from the area masking circuit 26. For example, the judge circuit 28 counts area masking signals of "1", and when a counted value exceeds a set value, the circuit 28 judges the bottle 12 defective and supplies a judge signal a conveyor system (not shown) of the bottle 12. In response to the judge signal the conveyor system removes the defective bottle.

A reference signal generator 30 generates a lens swing angle signal and an inspection period signal, based on a bottle position signal from a bottle position detector 32 provided on a rotary table 13 on which the bottle 12 is mounted. The lens swing angle signal is for swinging a concave lens 14a so that the transmitted light image of the bottle 12 is formed constantly on the two-dimensional photoelectric device 16 and is supplied to the lens drive circuit 21. The lens drive circuit 21 swings the concave lens 14a in accordance with a lens swing angle signal. The inspection period signal is indicative of a period in which the concave lens 14a is swinging in accordance with a movement of the bottle 12 and is supplied to the judge circuit 28.

Based on a lens swing angle signal from the reference signal generator 30, the lens drive circuit 21 drives the concave lens 14a. The lens drive circuit 21 performs feedback control based on a swing angle signal from the concave lens 14a as a feedback signal. When no swing angle signal is supplied by the concave lens 14a, the lens drive circuit 21 performs the control in the open loop.

An inspection period signal from the reference signal generator 30 is supplied to the judge circuit 28. The judge circuit 28 takes as effective only the defect detection signals which are inputted thereto in a period in which the inspection period signal is high level to judge whether or not the bottle 12 is defective. It is also possible to supply an inspection period signal to the inspection area/gate setting circuit 20, the defect detection circuit 24, and the continuous masking circuit 25 or the area masking circuit 26 and take as effective only the inspection period signals which are inputted to the judge circuit 28 in a period in which the inspection period signal is high level.

The monitor display RAM circuit 22 stores a digital image signal of the bottle 12 in a frame memory built therein to display the image on a monitor 36. The monitor display RAM circuit 22 has been supplied with a defect detection signal from the area masking circuit 26, a judge result signal from the judge circuit 28, and an inspection gate signal from the inspection area/gate setting circuit 20. Based on the defect detection signal, a defect point or an error scan are written in the monitor display RAM circuit 22. Based on the inspection gate signal, a corresponding inspection gate is displayed on the monitor 36.

As described above, the continuous masking is followed by the area masking. This enables a defect to be detected without any errors even when noises are generated due to an increase in the sensitivity. That is, this is because the continuous masking signals indicative of noises are isolated as shown in FIG. 6(a), While the continuous masking signals indicative of opaque defects, such as light smears, streaks, blisters, etc., are scattered as shown in FIG. 6(b), which enables noises and opaque defects to be discriminated from each other.

Figure 7:
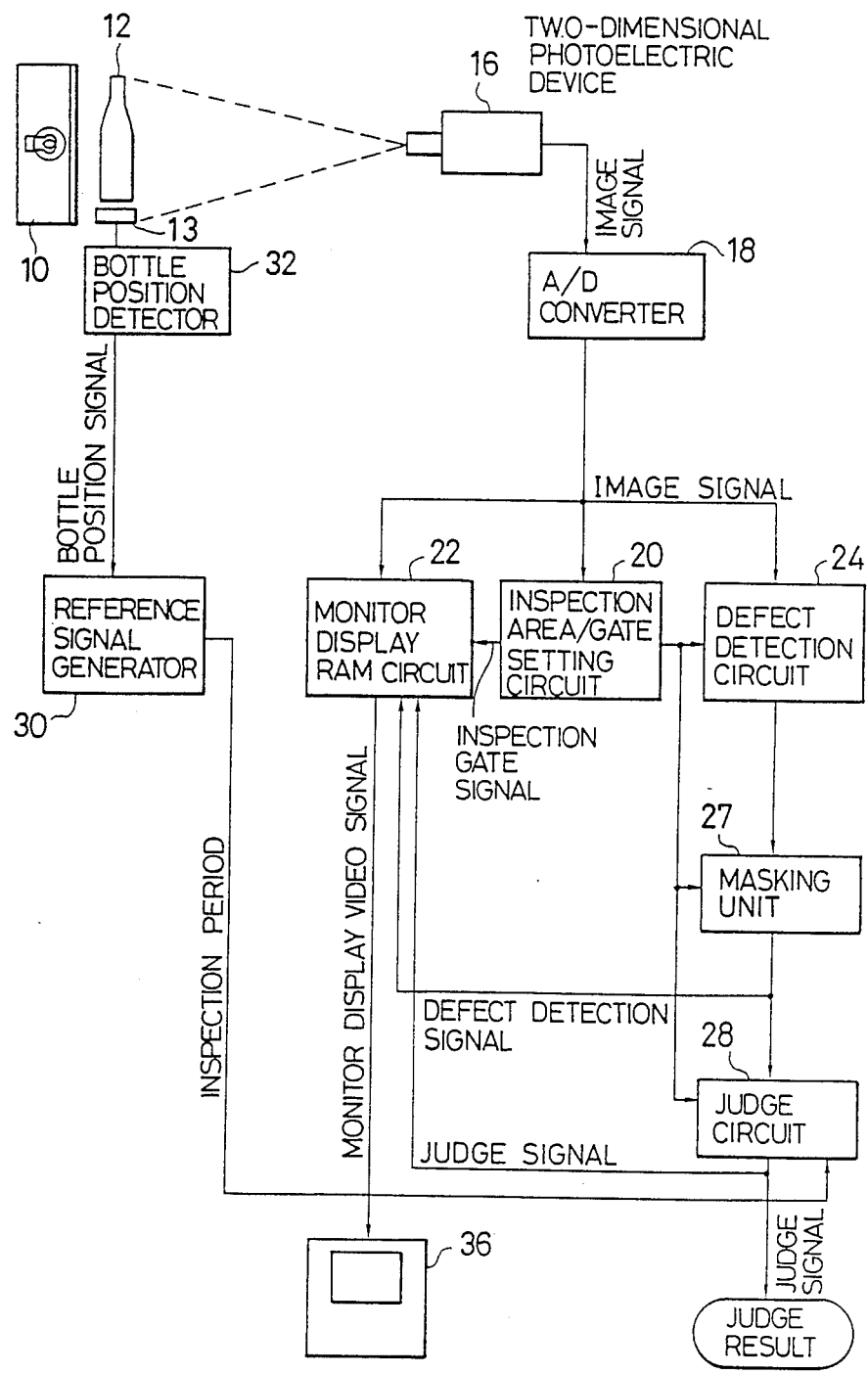
FIG. 7 is a block diagram of the apparatus for detecting defect on bottle sidewalls according to a second embodiment of this invention.

FIG. 7 shows the apparatus for detecting defects on bottle sidewalls according to a second embodiment of this invention. The members common with the first embodiment have share the same reference numerals not to repeat their explanations.

The second embodiment is characterized by a masking unit 27 for masking a defect detection signal from a defect detection circuit 24.

Figure 8:
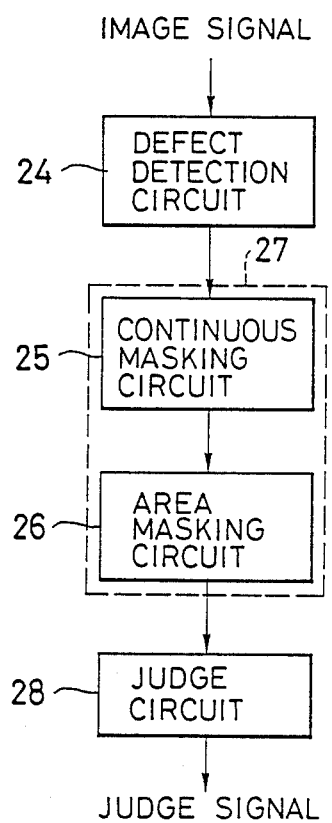
FIG. 8 is a block diagram of a masking unit of the apparatus for detecting defects on bottle sidewalls of FIG. 7.

The masking unit 27 of this embodiment is shown in FIG. 8 in good detail.

The masking unit 27 comprises a continuous masking circuit 26 and an area masking circuit 26. A defect detection signal from the defect detection circuit 24 is masked first by the continuous masking circuit 25, and then an output signal from the continuous masking circuit 25 is masked by the area masking circuit 26.

The continuous masking circuit 24 of this embodiment is the same as that of the first embodiment and omits as actually non-defects the defect points which are isolated or are continuous only below a set value to output a fresh continuous masking signal for each point.

Figure 9:
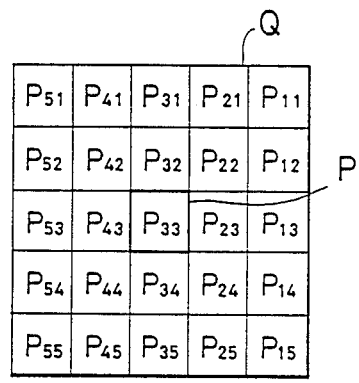
FIGS. 9 and 10 are views showing masking areas and smaller masking areas of the area masking of the apparatus for detecting defects on bottle sidewalls of FIG. 7.
Figure 10:
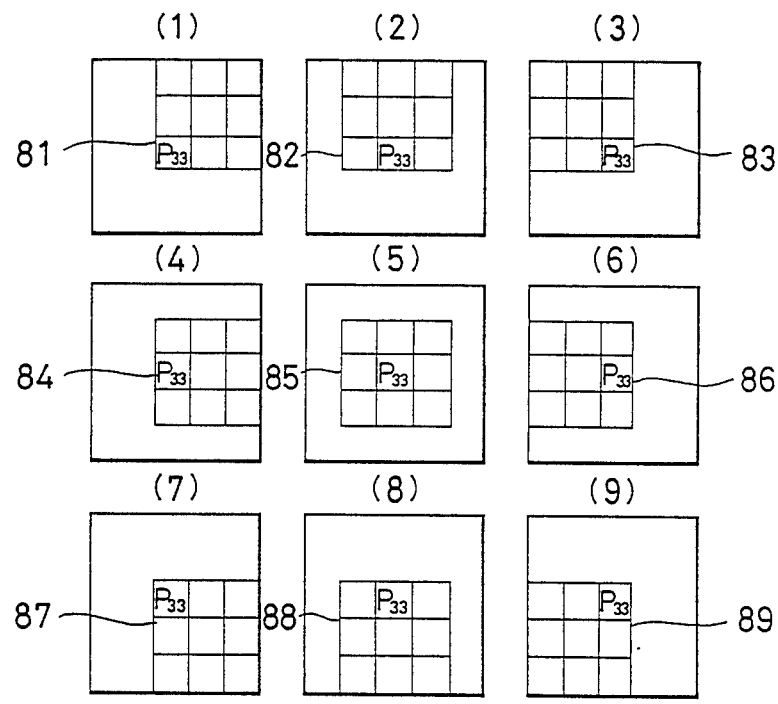

A continuous masking signal from the continuous masking circuit 25 is area-masked by the area masking circuit 26, and an area masking signal is outputted. In the area-masking, a rectangular masking area Q of 5 rows × 5 columns, for example, is set with a point to be noted (P33) centered as shown in FIG. 9. Further, as shown in FIG. 10, in the masking area Q are set smaller masking areas q1-q9 of, e.g., 3 rows × 3 columns with the point to be noted P33 contained. The numbers of defect points in the smaller masking areas q1-q9 are added, and when the total number of defect points in one of the smaller masking areas exceed a set value NR, and further the point to be noted P (P33) is a defect point, the point to be noted P (P33) is found a defect point.

Such area masking generates an area masking signal only at a portion where defect points indicated by continuous masking signals are concentrated, while noises, which are indicated by isolated defect points, are removed. Accordingly the contour of a defect which has been area-masked is not much changed.

An example of the area masking circuit 26 is shown in FIG. 11.

Continuous masking signals for respective images are inputted consecutively to a flip-flop 70 in synchronization with a clock signal φ and outputted. In the case of a 500 pixels × 500 pixels screen as shoWn in FIG. 5, for example, continuous masking signals are consecutively inputted in the flip-flop 70 first at the upper left end and vertically downward.

There are provided five RAMS 81, 82, 83, 84, 85 each having a capacity of 500 bits corresponding to the length of the vertical length of the screen. A number of the RAMs 81-85 corresponds to a number of columns of the masking area Q. Addresses to the RAMs 81-85 are generated by an address counter 72. Data are written in the RAMs 81-85 through respective write gates 81w-85w. It is designated by an output of a quinary ring counter 73 which write gate 81w-85w data is written in. The ring counter 73 counts up by one every time the address counter 72 has outputted addresses from 0 to 499.

The continuous masking signals retained by the flip-flop 70 are written in the one of the RAMs 81-85 designated by a ring counter 73 at bits of an address generated by an address counter 72. Accordingly, the RAMs 81-85 store continuous masking signals for adjacent 5 columns of the screen.

Continuous masking signals are read from the RAMs 81-85 through read gates 81r-85r. A continuous masking signal being currently written is read directly at a read gate 81r-85r associated with the one of the read gates 81r-85r designate by an output of a ring counter 73. At the other read gates 81r-85r, continuous masking signal are read from the associated RAMs 81-86. To give an example, when the ring counter 73 designates the read gate 81w, and a continuous masking signal is being written in the RAM 81, the continuous masking signal currently being written is read directly at the read gate 81r, while the continuous masking signals stored in the RAMs 82r-85r are read through read gates 82r-85r.

The continuous masking signals read through the read gates 81r-85r are re-arranged in order by a rearranging circuit 90 to be stored in respective 5-digit shift registers 91-95. A number of digits of the shift registers 91-95 corresponds to a number of columns of the masking area Q.

The re-arranging circuit 90 puts into another order the continuous masking signals read through the read gates 81r-85r based on an output from the ring counter 73 so that the outputs from the respective shift registers 91-95 are placed in a preset order of continuous masking signals as shown in FIG. 11.

By re-arranging continuous masking signals into another order by the re-arranging circuit 90, output signals form the shift registers 91-95 becomes continuous masking signals P11-P55 for the respective points of the masking area Q of FIG. 9.

There are provided adders 101-109 corresponding &o the smaller masking areas q1-q9 of FIG. 10, and the adders 101-109 add continuous masking signals P11-P55 for the points defining the respective smaller masking areas q1-q9 which are supplied by the shift registers 91-95. For example, the adder 101 adds the continuous masking signals P11, p12, P13, P21, P22, P23, P31, P32 and P33 which define the smaller masking area q1 of FIG. 10(1).

Addition results of the adders 101-109 are compared with a set value NR by comparators 111-119. A nine-input OR gate 120 gives a logical sum of comparison results of the comparators 111-119, and an AND gate gives a logical product of an output of the OR gate 120 with the continuous masking signal P33 of the point to be noted P. An output signal from the AND gate 121 is an area masking signal To be specific, in the case where the set value NR is 5, only when five or more points of one of the 3×3 smaller masking areas q1-q9 have continuous masking signals "1", and further the point to be noted P is a defect, the area masking signal becomes "1". Otherwise the area masking signal becomes "0".

The area masking circuit of FIG. 11 enables an area masking signal which has been given by area-masking a 5×5 masking area Q to be obtained in real time only by inputting consecutively continuous masking signals to the flip-flop 70.

A judge circuit 28 judges the presence of a defect, based on an area masking signal supplied by the area masking circuit 26.

In the embodiment described above, since whether or not a defect point is a defect is judged based on a number of defect points and a point to be noted in a smaller masking area, the area masking does not change the contour of a defect.

Figure 12:
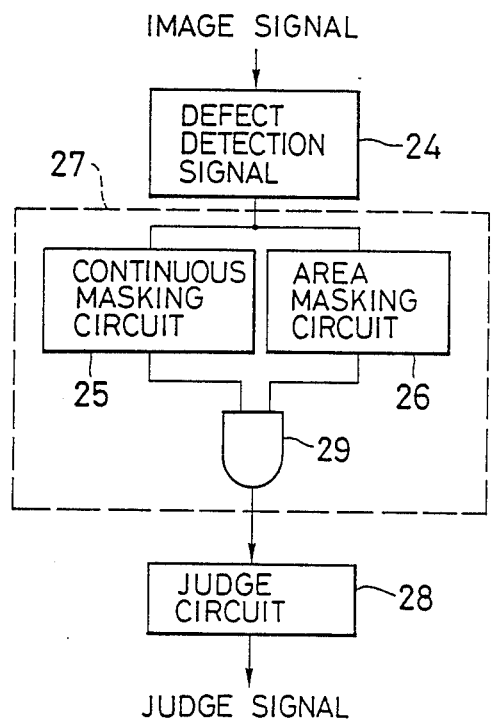
FIG. 12 is a block diagram of a first modification of the making unit of the apparatus for detecting defects on bottle sidewalls of FIG. 7.

FIG. 12 shows a first modification of the masking unit 27.

In this modification, a defect detection signal from the defect detection circuit 24 is supplied to the continuous masking unit 26 and the area masking circuit 26 so that the continuous masking the area-masking are performed parallelly. The continuous masking circuit 25 performs continuous masking on a defect detection signal to output a continuous masking signal, and the area masking circuit 26 performs the area-masking on the defect detection signal to output an area masking signal. An AND gate 29 gives a logical product of the continuous masking signal and an area masking signal of each point to supply an output signal to the judge circuit 28.

Figure 13:
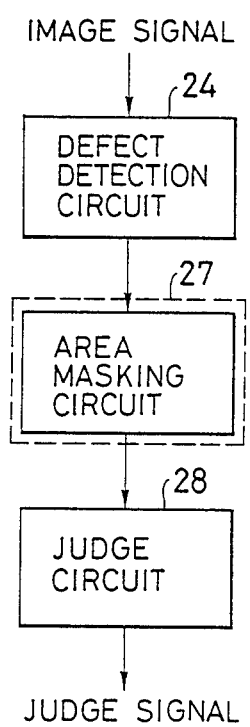
FIG. 13 is a block diagram of a second modification of the masking unit of the apparatus for detecting defect on bottle sidewalls of FIG. 7.

FIG. 13 shows a second modification of the masking unit 27.

In this modification, the masking unit 27 is provided by onlY an area masking circuit 27. The area masking circuit 27 area-masks a defect detection signal from the defect detection circuit 21 to output an area masking signal to the judge circuit 28.

This invention is not limited to the above-described embodiments and may cover variation which will be described beloW.

To give an example, in the above described first and second embodiments, the masking area Q for the area masking is 5 columns × 5 rows, and the smaller masking area q is 3 columns × 3 rows. These areas may be larger, e.g., the former may be 9 columns × 9 rows, and the latter being 5 columns × 5 rows.

Figure 14:
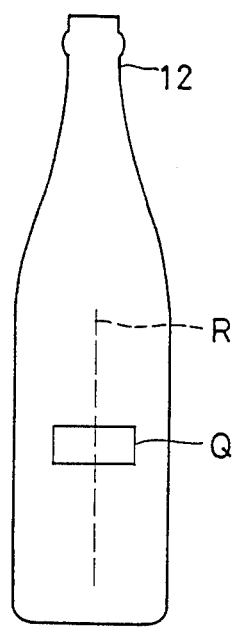
FIG. 14 is a view exemplifying the masking area.

The masking area Q and the smaller masking area q may be horizontally elongate or vertically elongate. For example, a horizontally elongate masking area Q exemplified in FIG. 14 prevents the erroneous detection of a joint R running vertically on the bottle 12 which was formed in manufacturing the bottle 12. That is, in the case where the direction of a matter, such as a joint R, which preferably is not detected as a defect is known beforehand, the masking area Q is set horizontal to the direction of the matter.

In the first embodiment, the bottle continuously conveyed is followed by changing the optical axis of the two-dimensional photoelectric device 16, but instead a mirror is used to follow the bottle 12.

In the second embodiment, the two dimensional photoelectric device 16 is used to detect a transmitted light image of the bottle 12, but instead a one dimensional photoelectric device, such as linear CCD, may be used.

This invention is usable in detecting defects on the surface of, e.g., metal parts, plastics, etc. other than bottles.

What is claimed is:

1. An apparatus for detecting defects on bottle sidewalls comprising:
    illumination means for illuminating the sidewall of a bottle;
    photoelectrically converting means for photoelectrically converting an image of lights transmitted through the sidewall of the bottle illuminated by the illuminating means;
    defect detecting means for inspecting the transmitted light image photoelectrically converted by the photoelectrically converting means for any defects to detect defects based on brightnesses of at least two points;
    area-masking means for setting a masking area corresponding to a point to be noted in the transmitted light image, and outputting an area-masking signal indicating that the point to be noted is a defect point when the number of defect points in the masking area is more that a set value; and
    judging means for judging the presence of a defect on the sidewall of the bottle, based on the area-masking signal from the area-masking means.

2. An apparatus for detecting defects on bottle sidewalls according to claim 1, wherein:
    the masking area set by the area masking means is a rectangular area of m columns x n rows;
    the area-masking means having
    an at least m-digit shift register for consecutively shifting signals for the respective points,
    a first adding circuit for adding defect points of the points stored in the shift register,
    at least n memories for consecutively storing an addition result of the first adding circuit,
    a second adding circuit for further adding the addition results stored in the n memories, and
    area masking signal generating means for generating an area masking signal based on an addition result of the second adding circuit.

3. An apparatus for detecting defects on bottle sidewalls according to claim 1, wherein
    there is further provided continuous masking means for finding whether or not the point to be noted is a defect point, based on continuity of said defect points, and outputting a continuous masking signal corresponding to respective points; and
    the are-masking means performs area masking, based on continuous masking signals for the respective points outputted by the continuous masking means.

4. An apparatus for detecting defects on bottle sidewalls according to claim 3, wherein:
    the masking area set by the area masking means is a rectangular area of m columns x n rows;
    the area-masking means having
    an at least m-digit shift register for consecutively shifting signals for the respective points,
    a first adding circuit for adding defect points of the points stored in the shift register,
    at least n memories for consecutively storing an addition result of the first adding circuit,
    a second adding circuit for further adding the addition results stored in the n memories, and
    area masking signal generating means for generating an area masking signal based on an addition result of the second adding circuit.

5. An apparatus for detecting defects on bottle sidewalls according to claim 1, wherein:
    the area-masking means sets in the masking area a plurality of smaller masking areas containing the point to be noted and being smaller than the masking area and finds the point to be noted a defect point when a number of defect points in one of the smaller masking areas is above a set value.

6. An apparatus for detecting defects on bottle sidewalls according to claim 5, wherein
    the area masking means finds the point to be noted a defect point when a number of defect points in one of the smaller masking areas is above a set value and further the point to be noted are defect points.

7. An apparatus for detecting defects on bottle sidewalls according to claim 5, wherein:
    the respective points in the masking area are contained in at least one of the smaller masking areas;
    those of the points in the masking area nearer to the point to be noted are contained in more smaller masking areas.

8. An apparatus for detecting defects on bottle sidewalls according to claim 6, wherein:
    the respective points in the masking area are contained in at least one of the smaller masking areas;
    those of the points in the masking area nearer to the point to be noted are contained in more smaller masking areas.

9. An apparatus for detecting defects on bottle sidewalls according to claim 6, wherein:
    there is further provided continuous masking means for finding whether or not the point to be noted is a defect point, based on continuity of said defect points, and outputting a continuous masking signal corresponding to respective points: and
    the area-masking means performs area masking, based on continuous masking signals for the respective points outputted by the continuous masking means.

10. An apparatus for detecting defects on bottle sidewalls according to claim 6, wherein:
    there is further provided continuous masking means for finding whether or not the point to be noted is a defect point, based on continuity of said defect points, and outputting a continuous masking signal corresponding to respective points; and
    the area-masking means performs area masking, based on continuous masking signals for the respective points outputted by the continuous masking means.

11. An apparatus for detecting defects on bottle sidewalls according to claim 7, wherein
there is further provided continuous masking means for finding whether or not the point to be noted is a defect point, based on continuity of said defect points, and outputting a continuous masking signal corresponding to respective points; and
the area-masking means performs area masking, based on continuous masking signals for the respective points outputted by the continuous masking means.

12. An apparatus for detecting defects on bottle sidewalls according to claim 8, wherein:
there is further provided continuous masking means for finding whether or not the point to be noted is a defect point, based on continuity of said defect points, and outputting a continuous masking signal corresponding to respective points: and
the area-masking means performs area masking, based on continuous masking signals for the respective points outputted by the continuous masking means.

13. An apparatus for detecting defects on bottle sidewalls according to claim 5, wherein:
there is provided continuous masking means for finding whether or not the point to be noted is a defect point, based on continuity of said defect points and outputting a continuous masking signal corresponding to respective points;
there is provided logical product means for giving a logical product a continuous masking signal from the continuous masking means, and area masking signals of the respective points; and
the judge means judges the presence of a defect on the sidewall of the bottle, based on a signal of the logical product from the logical product means.

14. An apparatus for detecting defects on bottle sidewalls according to claim 6, wherein:
there is provided continuous masking means for finding whether or not the point to be noted is a defect point, based on continuity of said defect points and outputting a continuous masking signal corresponding to respective points;
there is provided logical product means for giving a logical product a continuous masking signal from the continuous masking means, and area masking signals of the respective points; and
the judge means judges the presence of a defect on the sidewall of the bottle, based on a signal of the logical product from the logical product means.

15. An apparatus for detecting defects on bottle sidewalls according to claim 7, wherein:
there is provided continuous masking means for finding whether or not the point to be noted is a defect point, based on continuity of said defect points and outputting a continuous masking signal corresponding to respective points;
there is provided logical product means for giving a logical product a continuous masking signal from the continuous masking means, and area masking signals of the respective points; and
the judge means judges the presence of a defect on the sidewall of the bottle, based on a signal of the logical product from the logical product means.

16. An apparatus for detecting defects on bottle sidewalls according to claim 8, wherein:
there is provided continuous masking means for finding whether or not the point to be noted is a defect point, based on continuity of said defect points and outputting a continuous masking signal corresponding to respective points;
there is provided logical product means for giving a logical product a continuous masking signal from the continuous masking means, and area masking signals of the respective points; and
the judge means judges the presence of a defect on the sidewall of the bottle, based on a signal of the logical product from the logical product means.

17. An apparatus for detecting defects on bottle sidewalls according to claim 5, wherein:
the masking area is a rectangular area of m columns $\times$ n rows with the point to be noted centered;
$(m-k+1)\times(n-l+1)$ smaller masking areas are defined in each masking area;
a memory for storing signals of m column $\times$ n row points;
$(m-k+1)\times(n-l+1)$ adder circuits for reading signals of the points making up each said smaller masking area from the memory to add the same; and
$(m-k+1)\times(n-l+1)$ comparator circuits provided respectively in said adder circuits for comparing addition results of the adder circuits with said set value.

18. An apparatus for detecting defects on bottle sidewalls according to claim 6, wherein:
the masking area is a rectangular area of m columns $\times$ n rows with the point to be noted centered
$(m-k+1)\times(n-l+1)$ smaller masking areas are defined in each masking area;
a memory for storing signals of m column $\times$ n row points;
$(m-k+1)\times(n-l+1)$ adder circuits for reading signals of the points making up each said smaller masking area from the memory to add the same; and
$(m-k+1)\times(n-l+1)$ comparator circuits provided respectively in said adder circuits for comparing addition results of the adder circuits with said set value.

19. An apparatus for detecting defects on bottle sidewalls according to claim 7, wherein:
the masking area is a rectangular area of m columns $\times$ n rows with the point to be noted centered;
$(m-k+1)\times(n-l+1)$ smaller masking areas are defined in each masking area;
a memory for storing signals of m column $\times$ n row points;
$(m-k+1)\times(n-l+1)$ adder circuits for reading signals of the points making up each said smaller masking area from the memory to add the same;
$(m-k+1)\times(n-l+1)$ comparator circuits provided respectively in said adder circuits for comparing addition results of the adder circuits with said set value.

20. An apparatus for detecting defects on bottle sidewalls according to claim 8, wherein:
the masking area is a rectangular area of m columns $\times$ n rows with the point to be noted centered;
$(m-k+1)\times(n-l+1)$ smaller masking areas are defined in each masking area;
a memory for storing signals of m column $\times$ n row points;
$(m-k+1)\times(n-l+1)$ adder circuits for reading signals of the points making up each said smaller masking area from the memory to add the same; and $(m-k+1)\times(n-l+1)$ comparator circuits provided respectively in said adder circuits for comparing addition results of the adder circuits with said set value.

21. An apparatus for detecting defects on bottle sidewalls according to claim 9, wherein:
   the masking area is a rectangular area of m columns $\times$ n rows with the point to be noted centered;
   $(m-k+1)\times(n-l+1)$ smaller masking areas are defined in each masking area;
   a memory for storing signals of m column $\times$ n row points;
   $(m-k+1)\times(n-l+1)$ adder circuits for reading signals of the points making up each said smaller masking area from the memory to add the same; and
   $(m-k+1)\times(n-l+1)$ comparator circuits provided respectively in said adder circuits for comparing addition results of the adder circuits with said set value.

22. An apparatus for detecting defects on bottle sidewalls according to claim 10, wherein:
   the masking area is a rectangular area of m columns $\times$ n rows with the point to be noted centered;
   $(m-k+1)\times(n-l+1)$ smaller masking areas are defined in each masking area;
   a memory for storing signals of m column $\times$ n row points;
   $(m-k+1)\times(n-l+1)$ adder circuits for reading signals of the points making up each said smaller masking area from the memory to add the same; and
   $(m-k+1)\times(n-l+1)$ comparator circuits provided respectively in said adder circuits for comparing addition results of the adder circuits with said set value.

23. An apparatus for detecting defects on bottle sidewalls according to claim 11, wherein:
   the masking area is a rectangular area of m columns $\times$ n rows with the point to be noted centered;
   $(m-k+1)\times(n-l+1)$ smaller masking areas are defined in each masking area;
   a memory for storing signals of m column $\times$ n row points;
   $(m-k+1)\times(n-l+1)$ adder circuits for reading signals of the points making up each said smaller masking area from the memory to add the same; and
   $(m-k+1)\times(n-l+1)$ comparator circuits provided respectively in said adder circuits for comparing addition results of the adder circuits with said set value.

24. An apparatus for detecting defects on bottle sidewalls according to claim 12, wherein:
   the masking area is a rectangular area of m columns $\times$ n rows with the point to be noted centered;
   $(m-k+1)\times(n-l+1)$ smaller masking areas are defined in each masking area;
   a memory for storing signals of m column $\times$ n row points;
   $(m-k+1)\times(n-l+1)$ adder circuits for reading signals of the points making up each said smaller masking area from the memory to add the same;
   $(m-k+1)\times(n-l+1)$ comparator circuits provided respectively in said adder circuits for comparing addition results of the adder circuits with said set value.

25. An apparatus for detecting defects on bottle sidewalls according to claim 13, wherein:
   the masking area is a rectangular area of m columns $\times$ n rows with the point to be noted centered;
   $(m-k+1)\times(n-l+1)$ smaller masking areas are defined in each masking area;
   a memory for storing signals of m column $\times$ n row points;
   $(m-k+1)\times(n-l+1)$ adder circuits for reading signals of the points making up each said smaller masking area from the memory to add the same; and
   $(m-k+1)\times(n-l+1)$ comparator circuits provided respectively in said adder circuits for comparing addition results of the adder circuits with said set value.

26. An apparatus for detecting defects on bottle sidewalls according to claim 14, wherein:
   the masking area is a rectangular area of m columns $\times$ n rows with the point to be noted centered;
   $(m-k+1)\times(n-l+1)$ smaller masking areas are defined in each masking area;
   a memory for storing signals of m column $\times$ n row points;
   $(m-k+1)\times(n-l+1)$ adder circuits for reading signals of the points making up each said smaller masking area from the memory to add the same; and
   $(m-k+1)\times(n-l+1)$ comparator circuits provided respectively in said adder circuits for comparing addition results of the adder circuits with said set value.

27. An apparatus for detecting defects on bottle sidewalls according to claim 15, wherein:
   the masking area is a rectangular area of m columns $\times$ n rows with the point to be noted centered;
   $(m-k+1)\times(n-l+1)$ smaller masking areas are defined in each masking area;
   a memory for storing signals of m column $\times$ n row points;
   $(m-k+1)\times(n-l+1)$ adder circuits for reading signals of the points making up each said smaller masking area from the memory to add the same; and
   $(m-k+1)\times(n-l+1)$ comparator circuits provided respectively in said adder circuits for comparing addition results of the adder circuits with said set value.

28. An apparatus for detecting defects on bottle sidewalls according to claim 16, wherein:
   the masking area is a rectangular area of m columns $\times$ n rows with the point to be noted centered;
   $(m-k+1)\times(n-l+1)$ smaller masking areas are defined in each masking area;
   a memory for storing signals of m column $\times$ n row points;
   $(m-k+1)\times(n-l+1)$ adder circuits for reading signals of the points making up each said smaller masking area from the memory to add the same; and
   $(m-k+1)\times(n-l+1)$ comparator circuits provided respectively in said adder circuits for comparing addition results of the adder circuits with said set value.

* * * * *